United States Patent
Hiratsuka

(10) Patent No.: US 10,980,398 B2
(45) Date of Patent: Apr. 20, 2021

(54) CONNECTION BODY INCLUDING A WIRE FOR OPERATING AN ENDOSCOPE

(71) Applicant: OLYMPUS CORPORATION, Hachioji (JP)

(72) Inventor: Yoko Hiratsuka, Kodaira (JP)

(73) Assignee: OLYMPUS CORPORATION, Tokyo (JP)

( * ) Notice: Subject to any disclaimer, the term of this patent is extended or adjusted under 35 U.S.C. 154(b) by 418 days.

(21) Appl. No.: 15/943,252

(22) Filed: Apr. 2, 2018

(65) Prior Publication Data
US 2018/0220875 A1   Aug. 9, 2018

Related U.S. Application Data

(63) Continuation of application No. PCT/JP2016/079129, filed on Sep. 30, 2016.

(30) Foreign Application Priority Data

Oct. 7, 2015   (JP) .............................. JP2015-199664

(51) Int. Cl.
*A61B 1/00*        (2006.01)
*A61B 1/005*      (2006.01)
*G02B 23/24*      (2006.01)

(52) U.S. Cl.
CPC ........ *A61B 1/00071* (2013.01); *A61B 1/0011* (2013.01); *A61B 1/0057* (2013.01); *G02B 23/2476* (2013.01)

(58) Field of Classification Search
CPC combination set(s) only.
See application file for complete search history.

(56) References Cited

U.S. PATENT DOCUMENTS 6,193,717 B1 *  2/2001  Ouchi ............... A61B 18/1477
                                                                604/114
6,402,738 B1     6/2002  Ouchi
(Continued)

FOREIGN PATENT DOCUMENTS

JP       2000225121 A    8/2000
JP     20090233225 A   10/2009
(Continued)

OTHER PUBLICATIONS

International Search Report (ISR) dated Dec. 6, 2016 issued in International Application No. PCT/JP2016/079129.
(Continued)

*Primary Examiner* — Anh Tuan T Nguyen
*Assistant Examiner* — Shankar Raj Ghimire
(74) *Attorney, Agent, or Firm* — Holtz, Holtz & Volek PC

(57) ABSTRACT

A connection body includes: a wire for operating an endoscope; and a joint member having a cylindrical shape including a through hole into which the wire is inserted, the joint member being configured to be joined to an operating mechanism of the endoscope including an operating lever, the joint member including: a first cylindrical portion provided on a longitudinal rear end side of the joint member, a part of the first cylindrical portion being plastically deformed through pressurization to deform a part of the through hole such that the wire is fixed; and a second cylindrical portion provided on a front end side of the first cylindrical portion and having an outer diameter smaller than an outer diameter of the first cylindrical portion. The part of the first cylindrical portion plastically deformed is separated from the second cylindrical portion.

5 Claims, 6 Drawing Sheets

(56) References Cited

U.S. PATENT DOCUMENTS

| | | | | |
|---|---|---|---|---|
| 8,100,904 | B2* | 1/2012 | Sugita | A61B 17/320068 606/47 |
| 9,668,769 | B2* | 6/2017 | Kawaura | A61B 17/3417 |
| 9,899,750 | B1* | 2/2018 | Doiron | H01R 4/489 |
| 2004/0116833 | A1* | 6/2004 | Kato | D07B 3/00 600/585 |
| 2005/0143767 | A1* | 6/2005 | Kimura | A61B 17/1222 606/158 |
| 2007/0203487 | A1* | 8/2007 | Sugita | A61B 18/1492 606/45 |
| 2007/0282355 | A1* | 12/2007 | Brown | A61B 17/122 606/151 |
| 2008/0171911 | A1* | 7/2008 | Hanke | A61B 1/0011 600/138 |
| 2010/0200261 | A1* | 8/2010 | Boutot | H01R 43/048 174/19 |
| 2011/0207999 | A1* | 8/2011 | Torisawa | A61M 25/0136 600/114 |
| 2013/0289617 | A1* | 10/2013 | Suzuki | A61B 17/29 606/205 |
| 2013/0317291 | A1* | 11/2013 | Yamamoto | A61B 17/29 600/104 |
| 2015/0196286 | A1* | 7/2015 | Hatta | A61B 10/0283 600/581 |
| 2017/0086656 | A1 | 3/2017 | Hiratsuka | |

FOREIGN PATENT DOCUMENTS

| | | | |
|---|---|---|---|
| JP | 4928928 | B2 | 5/2012 |
| JP | 2014000209 | A * | 1/2014 |
| JP | 2014000209 | A | 1/2014 |
| JP | 2015177813 | A | 10/2015 |
| WO | 2016006516 | A1 | 1/2016 |

OTHER PUBLICATIONS

Written Opinion dated Dec. 6, 2016 issued in International Application No. PCT/JP2016/079129.

* cited by examiner ized to deform a part of the through hole such that the wire is fixed; and a second cylindrical portion provided on a front end side of the first cylindrical portion and having an outer diameter smaller than an outer diameter of the first cylindrical portion. The part of the first cylindrical portion plastically deformed is separated from the second cylindrical portion.

CONNECTION BODY INCLUDING A WIRE FOR OPERATING AN ENDOSCOPE

CROSS-REFERENCE TO RELATED APPLICATION

This application is a continuation of PCT International Application No. PCT/JP2016/079129 filed on Sep. 30, 2016 which claims the benefit of priority from Japanese Patent Application No. 2015-199664, filed on Oct. 7, 2015, the entire contents of which are incorporated herein by reference.

BACKGROUND

1. Technical Field

The present disclosure relates to a connection body.

2. Related Art

When using an endoscope inserted in an observation target or treatment target, by operating a wire for operating the endoscope (also referred to as an operation wire or angle wire) disposed inside an insertion portion, curving operation for a curve portion provided at the distal end of the insertion portion is performed. The distal end of the wire is assembled to the curve portion while the proximal end of the wire is assembled to an operating unit of the endoscope via a joint member. It is necessary to ensure that the joint member and the wire have durability for repetition. For this reason, techniques of soldering and fixing a joint member to a wire are known (see Japanese Patent No. 4928928, for example).

SUMMARY

In some embodiments, a connection body includes: a wire for operating an endoscope; and a joint member having a cylindrical shape including a through hole into which the wire is inserted, the joint member being configured to be joined to an operating mechanism of the endoscope including an operating lever, the joint member including: a first cylindrical portion provided on a longitudinal rear end side of the joint member, a part of the first cylindrical portion being plastically deformed through pressurization to deform a part of the through hole such that the wire is fixed; and a second cylindrical portion provided on a front end side of the first cylindrical portion and having an outer diameter smaller than an outer diameter of the first cylindrical portion. The part of the first cylindrical portion plastically deformed is separated from the second cylindrical portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, embodiments for practicing the disclosure (hereinafter referred to as "embodiments") will be described based on the accompanying drawings. The disclosure is not limited by the embodiments described below. In the different drawings, identical elements are provided with the same reference signs. It should be noted that the drawings are only schematic, and dimensional relations and ratios between the elements are different from actual ones. Dimensional relations and ratios between the elements in the different drawings may also be different from one another.

First Embodiment

Figure 1:
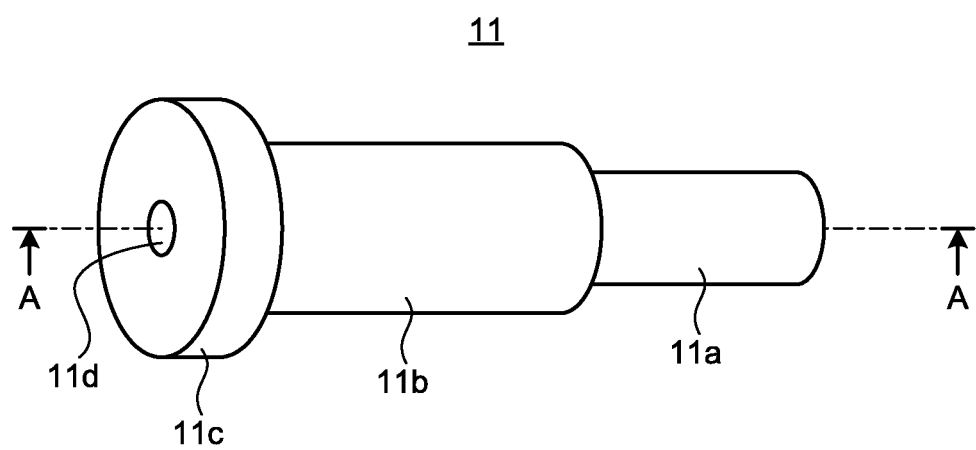
FIG. 1 is a perspective view illustrating an external configuration of a joint member according to a first embodiment.
Figure 2:
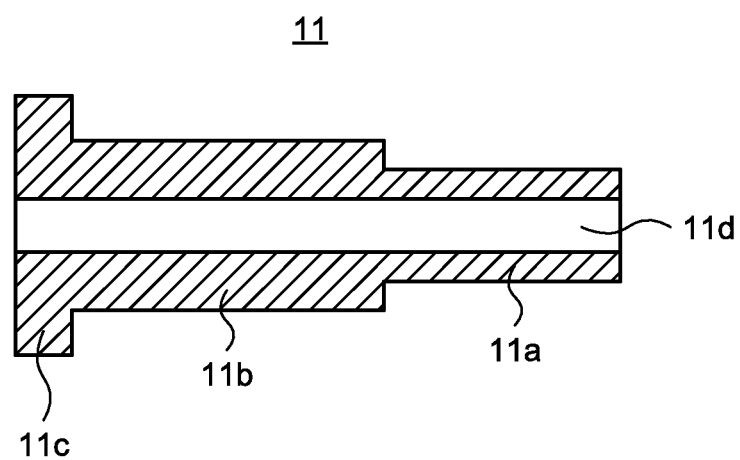
FIG. 2 is a cross-sectional view taken along line A-A of FIG. 1.

FIG. 1 is a perspective view illustrating an external configuration of a joint member applied to a connection structure according to a first embodiment. FIG. 2 is a cross-sectional view taken along line A-A of FIG. 1. A joint member 11 illustrated in FIGS. 1 and 2 is a member used for inserting one end portion of a wire for operating an endoscope into a through hole formed inside the joint member 11 and assembling it to an operating unit of the endoscope.

The joint member 11 includes a cylindrical small-diameter portion 11a, a cylindrical medium-diameter portion 11b, and a cylindrical large-diameter portion 11c. The medium-diameter portion 11b is provided on one height-directional end surface of the small-diameter portion 11a. The outer diameter of the medium-diameter portion 11b is larger than that of the small-diameter portion 11a, and the axis of the medium-diameter portion 11b coincides with that of the small-diameter portion 11a. The large-diameter portion 11c is provided on one height-directional end surface of the medium-diameter portion 11b which is different from the end surface linked to the small-diameter portion 11a. The outer diameter of the large-diameter portion 11c is larger than that of the medium-diameter portion 11b, and the axis of the large-diameter portion 11c coincides with that of the medium-diameter portion 11b. Hollow portions in the small-diameter portion 11a, the medium-diameter portion 11b, and the large-diameter portion 11c communicate with one another to form a through hole 11d passing through the joint member 11 in its axial direction. The inner diameter of the through hole 11d has a size that allows insertion of a wire to be joined.

The joint member 11 is assembled to an assembling member (described later) provided in the operating unit of the endoscope. The small-diameter portion 11a is assembled to the assembling member, with a connection member (described later) attached to the outer periphery thereof. The medium-diameter portion 11b is plastically deformed through swaging to secure the wire inserted in the through hole 11d, and is assembled to the assembling member in this state.

The joint member 11 is made of metal such as brass, for example. Hereinafter, the side where the small-diameter portion 11a is positioned along the longitudinal direction of the joint member 11 (the right side of the joint member 11 in FIG. 1) is referred to as a front end side, and the side where the large-diameter portion 11c is positioned along the longitudinal direction of the joint member 11 (the left side of the joint member 11 in FIG. 1) is referred to as a rear end side.

Next, a method of connecting the joint member 11 having the above-described configuration to a wire will be described. First, a wire is inserted into the through hole 11d of the joint member 11. The wire is inserted into the through hole 11d from the front end side of the joint member 11 until the end portion of the wire comes out from the rear end side of the joint member 11. The wire is, for example, a stainless steel stranded wire.

Figure 3:
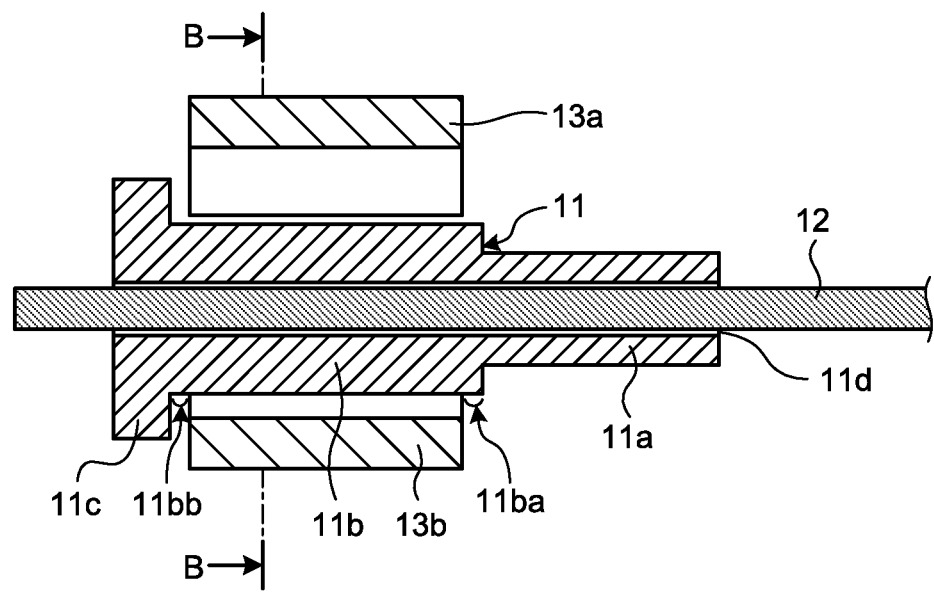
FIG. 3 is a cross-sectional view illustrating how the joint member with a wire for operating an endoscope inserted therein is installed in a swaging device.
Figure 4:
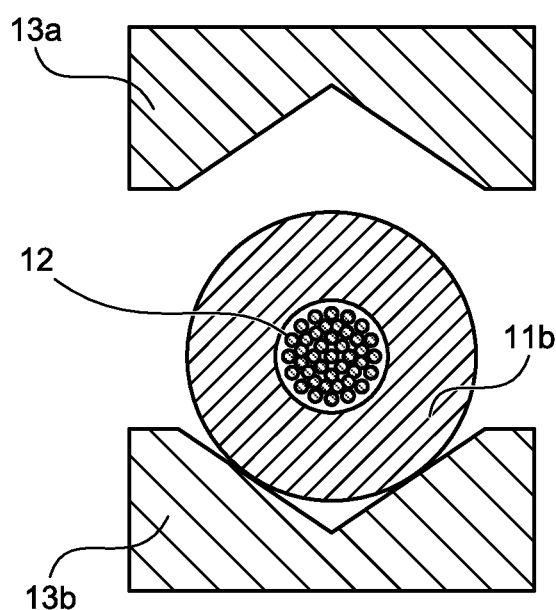
FIG. 4 is a cross-sectional view taken along line B-B of FIG. 3 and illustrating a plane orthogonal to the longitudinal direction of the joint member as a cutting plane.

Subsequently, the joint member 11 with the wire inserted therein is installed in a swaging device to be subjected to swaging. FIG. 3 is a cross-sectional view illustrating how the joint member 11 with a wire 12 for operating an endoscope inserted therein is installed in a swaging device. FIG. 4 is a cross-sectional view taken along line B-B of FIG. 3 and illustrating a plane orthogonal to the longitudinal direction of the joint member 11 as a cutting plane. Before swaging is performed, the medium-diameter portion 11b of the joint member 11 is arranged between a pair of metal molds 13a and 13b of the swaging device. The axial length of the medium-diameter portion 11b is set to be slightly longer than the axial length of each of the metal molds 13a and 13b. The medium-diameter portion 11b is arranged between the pair of metal molds 13a and 13b in such a manner that non-contact portions 11ba and 11bb that are not in contact with the metal molds 13a and 13b are provided on opposite axial sides of the medium-diameter portion 11b. It is more preferable that the two non-contact portions 11ba and 11bb be equal in longitudinal length.

As illustrated in FIG. 4, each of the metal molds 13a and 13b has a V-shaped cross section. In response to a processing start signal being sent to the swaging device to activate the swaging device, either of the metal molds 13a and 13b (metal mold 13a in FIGS. 3 and 4) moves toward the other metal mold (metal mold 13b in FIGS. 3 and 4) to pressurize and plastically deform the medium-diameter portion 11b. As a result of the plastic deformation, the part of the through hole 11d positioned inside the medium-diameter portion 11b is deformed, the cross-sectional shape of the wire 12 inside the through hole 11d is deformed to be flat, and the wire strands on the outer periphery thereof bite the inner wall of the through hole 11d. Consequently, the joint member 11 is fixed to the wire 12.

After that, one metal mold (metal mold 13a in FIG. 4) is returned to the position before pressurization, the medium-diameter portion 11b is released, and the series of processes is completed. Thus, the fabrication of a connection body including the joint member 11 and the wire 12 is completed.

Figure 5:
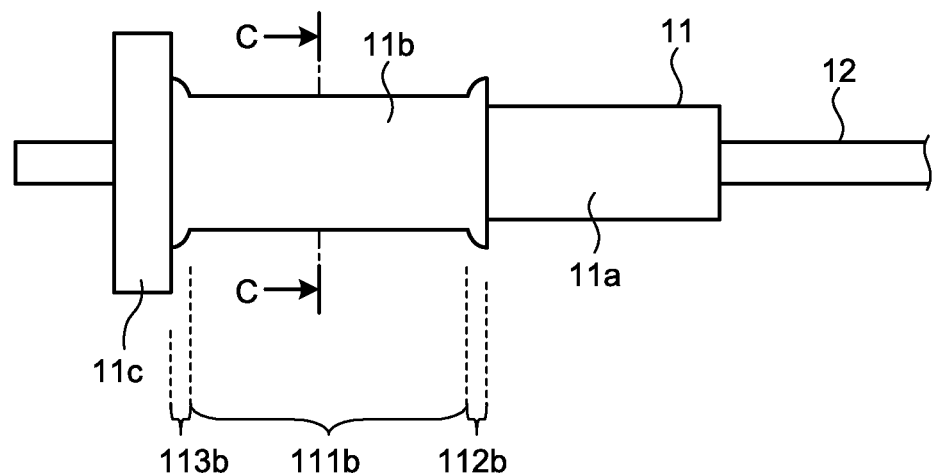
FIG. 5 is a side view illustrating a configuration of a connection body having a connection structure according to the first embodiment.
Figure 6:
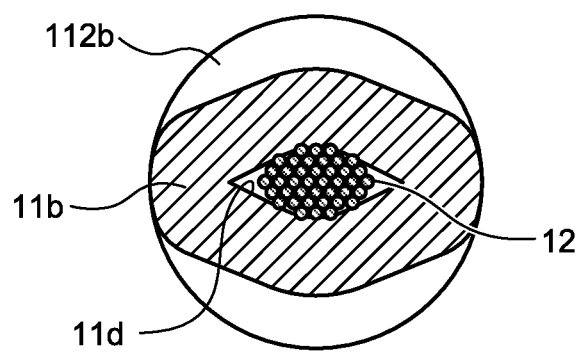
FIG. 6 is a cross-sectional view taken along line C-C of FIG. 5.

FIG. 5 is a side view illustrating a configuration of the connection body fabricated using the above-described connection method. FIG. 6 is a cross-sectional view taken along line C-C of FIG. 5. In a connection body 100 illustrated in FIGS. 5 and 6, the medium-diameter portion 11b (first cylindrical portion) of the joint member 11 has a swaged portion 111b and end portions 112b and 113b. The cross section of the swaged portion 111b is plastically deformed in a substantially rhombic shape through swaging. The end portions 112b and 113b are positioned on opposite axial end sides of the swaged portion 111b, and at least the end surface of each of the end portions 112b and 113b which is not in contact with the swaged portion 111b is not plastically deformed. As illustrated in FIG. 6, the outer shape of the wire 12 positioned inside the swaged portion 111b is deformed to be flat as the swaged portion 111b is plastically deformed. Although a part of each of the end portions 112b and 113b which is in contact with the swaged portion 111b is plastically deformed as the swaged portion 111b is deformed, the region around the end surface of each of the end portions 112b and 113b which is not in contact with the swaged portion 111b is not plastically deformed but maintains the shape before swaging (see FIG. 4). In other words, the plastically deformed part of the medium-diameter portion 11b is separated from the small-diameter portion 11a (second cylindrical portion) which is a non-plastically deformed part. In addition, the small-diameter portion 11a, the large-diameter portion 11c (third cylindrical portion), and the part of the wire 12 passing therethrough also maintain the original shapes without being plastically deformed after swaging.

Figure 7:
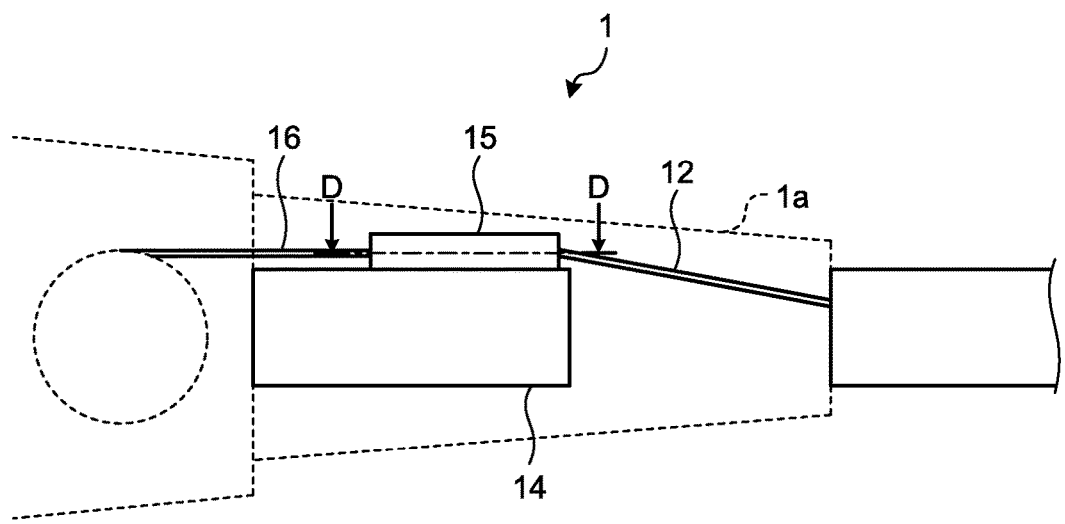
FIG. 7 is a schematic view illustrating how the connection body is assembled to an operating unit of an endoscope.

FIG. 7 is a schematic view illustrating how the connection body 100 is assembled to the operating unit of the endoscope. As illustrated in FIG. 7, a operating unit 1 of the endoscope includes a supporting member 14, an assembling member 15, and a chain 16. The assembling member 15 is movably provided in contact with the supporting member 14, and the connection body 100 is assembled to the assembling member 15. The chain 16 is connected to the rear end side of the assembling member 15 (left side in FIG. 7). These parts are accommodated inside an outer casing 1a of the operating unit 1. The wire 12 of the connection body 100 extends in an oblique direction with respect to the longitudinal direction (axial direction) of the assembling member 15 inside the outer casing 1a, and is disposed at a predetermined part in an insertion portion of the endoscope. The other end of the chain 16 is connected to an internal mechanism of the operating unit 1, and the distal end portion of the chain 16 connected to the assembling member 15 moves along the extending direction thereof according to the operation for the operating unit 1. The wire 12 assembled to the assembling member 15 moves as the chain 16 moves, thereby realizing curving operation for a curve portion at the distal end of the endoscope.

Figure 8:
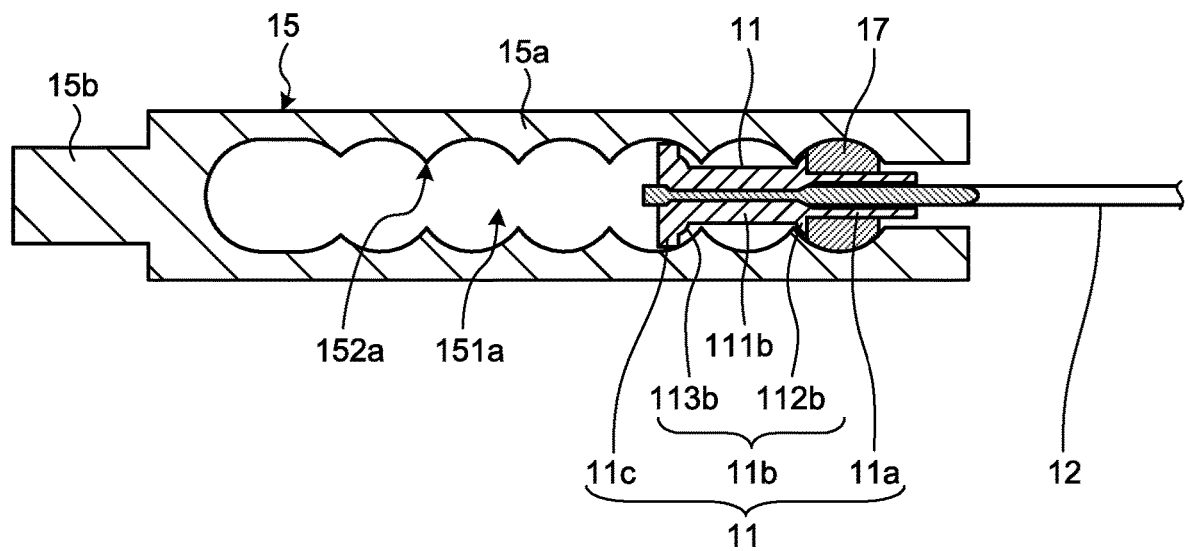
FIG. 8 is a cross-sectional view taken along line D-D of FIG. 7.

FIG. 8 is a cross-sectional view taken along line D-D of FIG. 7 and illustrating a configuration of the assembling member 15 and a mode of assembling the connection body 100 to the assembling member 15. The assembling member 15 has a holding portion 15a and a joint portion 15b. The holding portion 15a has a substantially rectangular parallelepiped shape and holds the connection body 100. The joint portion 15b extends from the longitudinal end portion of the holding portion 15a, and the chain 16 is connected to the joint portion 15b.

In the holding portion 15a, a hollow portion 151a extending in the longitudinal direction is formed. One longitudinal end portion of the hollow portion 151a opposite to the longitudinal end portion provided with the joint portion 15b is opened, and one side surface of the hollow portion 151a is opened. The cross section illustrated in FIG. 8 has the same shape as the one side surface of the holding portion 15a in which the hollow portion 151a is opened. The hollow portion 151a has the same cross-sectional shape anywhere along the direction perpendicular to the paper surface of FIG. 8. In FIG. 7, the opening formed in the one side surface of the holding portion 15a faces the supporting member 14, so it does not appear in the drawing.

In the cross section illustrated in FIG. 8, the maximum width of the hollow portion 151a in the direction orthogonal to the longitudinal direction is slightly larger than the outer diameter of the large-diameter portion 11c of the joint member 11. In the cross section illustrated in FIG. 8, the hollow portion 151a includes, at predetermined intervals along the longitudinal direction, narrow portions 152a having the narrowest width in the direction orthogonal to the longitudinal direction. In the cross section illustrated in FIG. 8, the hollow portion 151a has a substantially circular cross section between adjacent narrow portions 152a, and the diameter of the circle corresponds to the maximum width described above. The width of each of the narrow portions 152a is slightly larger than the outer diameter of the swaged portion 111b formed on the medium-diameter portion 11b of the joint member 11. The longitudinal interval between adjacent narrow portions 152a is slightly shorter than the length of the swaged portion 111b. By setting the size of the hollow portion 151a in this way, it is possible to accommodate the connection body 100 in the hollow portion 151a.

The first thing to do in order to assemble the connection body 100 to the assembling member 15 is to attach, to the outer periphery of the small-diameter portion 11a of the joint member 11, a connection member 17 having a shape capable of being fit into the hollow portion 151a of the holding portion 15a. The connection member 17 has a columnar shape and has a height substantially equal to the depth of the hollow portion 151a in the depth direction (direction orthogonal to the cross section of FIG. 8). A cross section parallel to the height direction of the connection member 17 has such a shape that the substantially circular shape of the cross section between adjacent narrow portions 152a in FIG. 8 is cut around the narrow portions 152a along the width direction (up-down direction in FIG. 8). A through hole into which the small-diameter portion 11a of the joint member 11 can be inserted is formed in the height-directional center of the connection member 17.

Subsequently, the connection body 100 is fit in a predetermined position inside the hollow portion 151a from the one open side surface of the holding portion 15a. Specifically, the connection body 100 and the assembling member 15 are aligned so that the opening in the longitudinal end surface of the holding portion 15a is oriented in the same direction as the wire 12 extending toward the distal end portion. Then, the connection member 17 is located in any of the positions inside the hollow portion 151a where the connection member 17 can be fit (position between adjacent narrow portions 152a). After that, the joint member 11 is fit into the hollow portion 151a of the holding portion 15a. As a result, the holding portion 15a holds the connection body 100 as illustrated in FIG. 8. In this state, the connection body 100 is rotatable around the axis of the joint member 11.

The assembling position of the connection body 100 can be changed by changing the fitting position of the connection member 17 inside the hollow portion 151a. Therefore, the connection member 17 has a function of adjusting the longitudinal position of the joint member 11. In addition, since the connection member 17 has a width larger than the outer diameter of the end portion 112b in the cross section illustrated in FIG. 8, the connection member 17 also has a function of preventing disengagement of the joint member 11 in the axial direction.

As described above, the assembling member 15 is arranged inside the operating unit 1 such that the opening in the side surface faces the supporting member 14 after the connection body 100 is assembled. Consequently, it is possible to prevent the connection body 100 from falling off through the opening in the side surface of the assembling member 15.

According to the first embodiment described above, one end portion of the wire 12 is inserted into the through hole 11d formed in the joint member 11 from the longitudinal front end portion to the longitudinal rear end portion. A part of the rear end portion is plastically deformed so that the one end portion of the wire 12 inserted in the through hole 11d is secured to the joint member 11, and a non-plastically deformed part is formed at the front end portion. Therefore, it is possible to realize a highly durable connection between the wire for operating the endoscope and the joint member without using solder.

In the first embodiment, only the wire 12 in the swaged portion 111b is deformed to be flat after the joint member 11 is subjected to swaging, and the small-diameter portion 11a, the large-diameter portion 11c, and the wire 12 positioned therein are not deformed. Therefore, as illustrated in FIG. 7, even when the wire 12 is assembled in such a manner as to extend in a direction intersecting the longitudinal direction of the joint member 11, no radial force is applied to the flattened wire 12 in the swaged portion 111b. Therefore, it is possible to prevent the wire 12 inside the swaged portion 111b from triggering deterioration, and to ensure the durability of the wire 12.

Further, in the first embodiment, by providing the end portions 112b and 113b for alleviating the deformation due to swaging at opposite axial ends of the medium-diameter portion 11b of the joint member 11, the small-diameter portion 11a and the large-diameter portion 11c can be prevented from being deformed through swaging, and the joint member 11 can be securely assembled to the assembling member 15 and the connection member 17.

In addition, in the first embodiment, since the joint member 11 is connected to the wire 12 through swaging instead of soldering that requires a high level of skill, it is possible to efficiently fabricate the connection body 100 having stable quality irrespective of the skill of an operator. Accordingly, in the first embodiment, the step of washing flux is unnecessary, and the lead time can be shortened.

Second Embodiment

Figure 9:
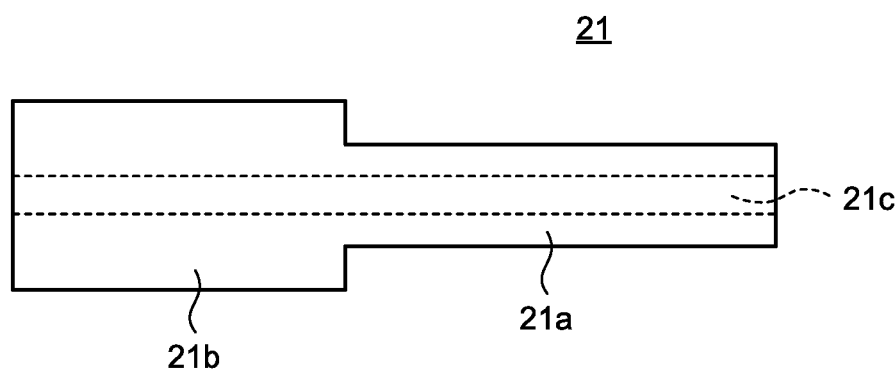
FIG. 9 is a side view of a joint member according to a second embodiment.

FIG. 9 is a side view illustrating a configuration of a joint member according to a second embodiment. A joint member 21 illustrated in FIG. 9 has a cylindrical small-diameter portion 21a and a cylindrical large-diameter portion 21b. The outer diameter of the large-diameter portion 21b is larger than that of the small-diameter portion 21a, and the axis of the large-diameter portion 21b coincides with that of the small-diameter portion 21a. Hollow portions in the small-diameter portion 21a and the large-diameter portion 21b communicate with each other to form a through hole 21c passing through the joint member 21 in its axial direction. The inner diameter of the through hole 21c has a size that allows insertion of a wire to be joined. Like the joint member 11, the joint member 21 is made of metal such as brass. Hereinafter, the side where the small-diameter portion 21a is positioned along the longitudinal direction of the joint member 21 (the right side of the joint member 21 in FIG. 9) is referred to as a front end side, and the side where the large-diameter portion 21b is positioned along the longitudinal direction of the joint member 21 (the left side of the joint member 21 in FIG. 9) is referred to as a rear end side.

The small-diameter portion 21a is assembled to an assembling member (described later), with the connection member 17 attached to the outer periphery thereof. The large-diameter portion 21b is plastically deformed through swaging to secure the wire inserted in the through hole 21c, and is assembled to the assembling member in this state.

Next, a method of connecting the joint member 21 having the above-described structure to a wire will be described. First, a wire is inserted into the through hole 21c of the joint member 21. The wire is inserted into the through hole 21c from the front end side of the joint member 21 until the end portion of the wire comes out from the rear end side of the joint member 21. The wire is, for example, a stainless steel stranded wire.

Subsequently, the joint member 21 with the wire inserted therein is installed in a swaging device to be subjected to swaging. In the second embodiment, the large-diameter portion 21b is arranged between a pair of metal molds of the swaging device. The axial length of the large-diameter portion 21b is set to be slightly longer than the axial length of each of the metal molds. The large-diameter portion 21b is arranged between the pair of metal molds in such a manner that a non-contact portion that is not in contact with the pair of metal molds is provided near the small-diameter portion 21a. For example, the metal molds 13a and 13b described in the first embodiment can be used as the pair of metal molds. By performing swaging in the same manner as in the first embodiment, the large-diameter portion 21b is plastically deformed, the part of the through hole 21c positioned inside the large-diameter portion 21b is deformed, the outer shape of the wire inside the through hole 21c is deformed to be flat, and the wire strands on the outer periphery thereof bite the inner wall of the through hole 21c. Consequently, the joint member 21 is connected to the wire.

Figure 10:
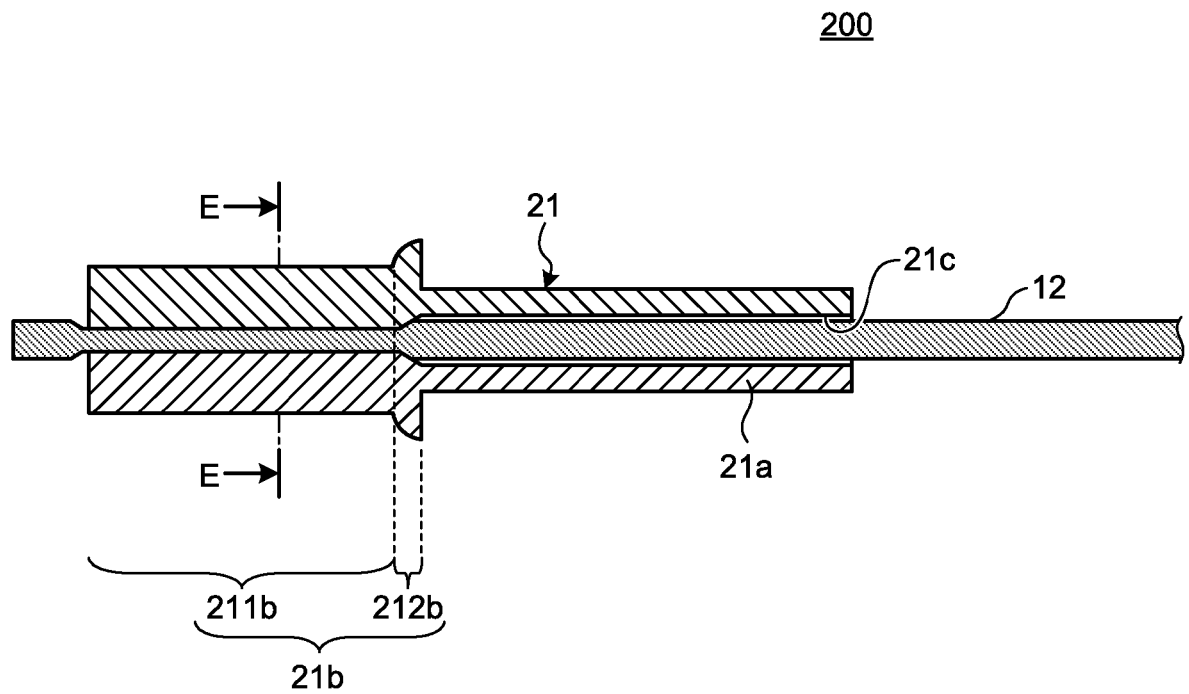
FIG. 10 is a side view illustrating a configuration of a connection body having a connection structure according to the second embodiment.

FIG. 10 is a cross-sectional view illustrating a configuration of a connection body formed using the above-described connection method. A connection body 200 illustrated in FIG. 10 is formed through swaging using the pair of metal molds 13a and 13b described in the first embodiment.

As illustrated in FIG. 10, the large-diameter portion 21b (first cylindrical portion) of the joint member 21 has a swaged portion 211b and an end portion 212b. The cross section of the swaged portion 211b is deformed in a substantially rhombic shape through swaging. The end portion 212b is positioned on the axial front end side of the swaged portion 211b, and at least the end surface of the end portion 212b which is not in contact with the swaged portion 211b is not deformed. The wire 12 positioned inside the swaged portion 211b is deformed to be flat as the swaged portion 211b is plastically deformed. The cross section taken along line E-E of FIG. 10 has the same shape as the cross section illustrated in FIG. 6. Although a part of the end portion 212b which is in contact with the swaged portion 211b is deformed as the swaged portion 211b is deformed, the region around the end surface of the end portion 212b which is not in contact with the swaged portion 211b is not deformed but maintains the shape before swaging (see FIG. 9). In other words, the plastically deformed part of the large-diameter portion 21b is separated from the small-diameter portion 21a (second cylindrical portion) which is a non-plastically deformed part. In addition, the small-diameter portion 21a and the part of the wire 12 passing therethrough also maintain the original shapes without being plastically deformed.

Figure 11:
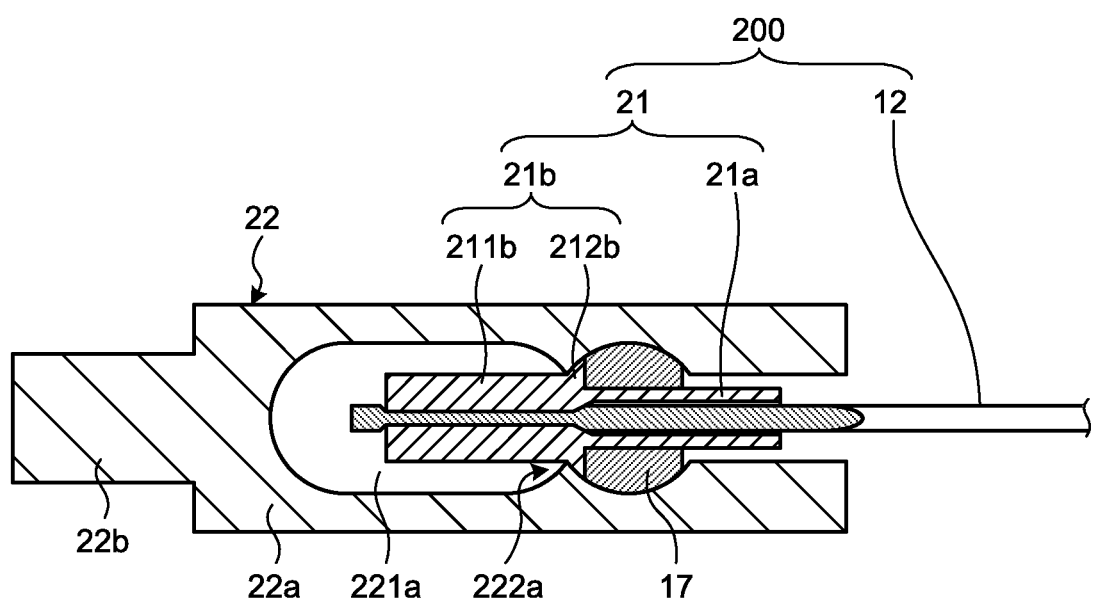
FIG. 11 is a view illustrating a configuration of an assembling member and a mode of assembling the connection body to the assembling member.

FIG. 11 is a cross-sectional view at a cutting plane similar to that in FIG. 8 illustrating a configuration of the assembling member and a mode of assembling the connection body 200 to the assembling member. The manner in which the assembling member with the connection body 200 assembled thereto is installed in the operating unit of the endoscope is similar to that in FIG. 8.

An assembling member 22 illustrated in FIG. 11 has a holding portion 22a and a joint portion 22b. The holding portion 22a has a substantially rectangular parallelepiped shape and holds the connection body 200. The joint portion 22b extends from the longitudinal end portion of the holding portion 22a, and the chain 16 is connected to the joint portion 22b.

In the holding portion 22a, a hollow portion 221a extending in the longitudinal direction is formed. One longitudinal end portion of the hollow portion 221a opposite to the longitudinal end portion provided with the joint portion 22b is opened, and one side surface of the hollow portion 221a is opened. The cross section illustrated in FIG. 11 has the same shape as the one side surface of the holding portion 22a in which the hollow portion 221a is opened. The hollow portion 221a has the same cross-sectional shape anywhere along the direction perpendicular to the paper surface of FIG. 11.

In the cross section illustrated in FIG. 11, the hollow portion 221a includes a narrow portion 222a having the narrowest width in the direction orthogonal to the longitudinal direction. In the cross section illustrated in FIG. 11, the hollow portion 221a has a substantially circular cross section on the opening side of the narrow portion 222a so that the connection member 17 can be fit thereinto. The width of the narrow portion 222a is slightly larger than the outer diameter of the swaged portion 211b formed on the large-diameter portion 21b of the joint member 21. By setting the size of the hollow portion 221a in this way, it is possible to accommodate the connection body 200 in the hollow portion 221a.

The method of assembling the connection body 200 to the assembling member 22 is the same as the method of assembling the connection body 100 to the assembling member 15 described in the first embodiment. The connection body 200 is assembled to the assembling member 22 in such a manner as to be rotatable around the axis of the joint member 21.

As in the first embodiment, the connection member 17 according to the second embodiment has a function of preventing disengagement of the joint member 21 in the axial direction.

According to the above-described second embodiment, as in the first embodiment, it is possible to realize a highly durable connection between the wire for operating the endoscope and the joint member without using solder.

Further, in the second embodiment, only the wire 12 in the swaged portion 211b is deformed to be flat after the joint member 21 is subjected to swaging, and the small-diameter portion 21a and the wire 12 positioned therein are not deformed. Therefore, as in the first embodiment, it is possible to prevent the wire 12 inside the swaged portion 211b from triggering deterioration, and to ensure the durability of the wire 12.

Further, according to the second embodiment, as in the first embodiment, the joint member 21 can be connected to the wire 12 through swaging, and by providing the end portion 212b, the small-diameter portion 21a can be prevented from being deformed through swaging, and the joint member 21 can be securely assembled to the assembling member 22 and the connection member 17.

The disclosure is not limited only to the above-mentioned first and second embodiments. A plurality of components disclosed in the respective embodiments can be appropriately combined to conceive various inventions.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A connection body comprising:
   a wire for operating an endoscope; and
   a joint member having a cylindrical shape including a through hole into which the wire is inserted, the joint member being configured to be joined to an operating mechanism of the endoscope, the joint member including: (i) a first cylindrical portion provided on a longitudinal rear end side of the joint member, and (ii) a second cylindrical portion provided on a front end side of the first cylindrical portion and having an outer diameter that is smaller than an outer diameter of the first cylindrical portion, the second cylindrical portion being configured to have a member of the endoscope attached to an outer periphery of the second cylindrical portion,
   wherein a part of the first cylindrical portion is plastically deformed by pressure to deform a part of the through hole such that the wire inserted into the through hole is fixed to an inner surface of the deformed through hole, and the part of the first cylindrical portion that is plastically deformed is arranged at an interval from the second cylindrical portion along a direction in which the wire extends, and
   wherein the first cylindrical portion includes first and second parts that are not plastically deformed, and are arranged at proximal and distal sides, respectively, of the part of the first cylindrical portion that is plastically deformed.

2. The connection body according to claim 1, further comprising a third cylindrical portion provided on a rear end side of the first cylindrical portion and having an outer diameter that is larger than the outer diameter of the first cylindrical portion,
   wherein the part of the first cylindrical portion that is plastically deformed is arranged at an interval from the third cylindrical portion along the direction in which wire extends.

3. The connection body according to claim 2, wherein the second and third cylindrical portions are not plastically deformed.

4. The connection body according to claim 1, wherein the second cylindrical portion is not plastically deformed.

5. The connection body according to claim 1, wherein the second part of the first cylindrical portion, which is not plastically deformed and is arranged at the distal side of the part of the first cylindrical portion that is plastically deformed, is adjacent to the second cylindrical portion.

\* \* \* \* \*